United States Patent
Antoine et al.

(10) Patent No.: US 6,541,027 B1
(45) Date of Patent: Apr. 1, 2003

(54) LACTIC ACID BACTERIA WITH ANXIOLYTIC PROPERTIES AND USES THEREOF

(75) Inventors: Jean-Michel Antoine, Maisons-Alfort (FR); Chantal Cayuela, Paris (FR); Marie-Christine Degivry, Le Plessis Robinson (FR); Christian Latge, Igny (FR); Eric Postaire, Vanves (FR)

(73) Assignee: Compagnie Gervais Danone, Levallois-Perret (FR)

( * ) Notice: Subject to any disclaimer, the term of this patent is extended or adjusted under 35 U.S.C. 154(b) by 0 days.

(21) Appl. No.: 10/009,086
(22) PCT Filed: May 5, 2000
(86) PCT No.: PCT/FR00/01238

§ 371 (c)(1),
(2), (4) Date: Feb. 11, 2002

(87) PCT Pub. No.: WO00/67696
PCT Pub. Date: Nov. 16, 2000

(30) Foreign Application Priority Data

May 6, 1999 (FR) .............................. 99 05760

(51) Int. Cl.$^7$ .......................... A61K 35/74; A61K 35/20
(52) U.S. Cl. ...................... 424/439; 424/535; 424/780; 426/7; 426/34; 435/42; 435/252.1; 435/252.4; 435/253.4; 435/854; 435/885
(58) Field of Search ............................... 435/252.1, 42, 435/253.4, 252.4, 854, 885; 426/34, 7; 424/439, 535, 780

(56) References Cited

FOREIGN PATENT DOCUMENTS

| | | |
|---|---|---|
| EP | 0 652 285 A2 | 5/1995 |
| EP | 1 016 709 A1 | 9/1997 |
| EP | 0 966 969 A1 | 12/1999 |
| JP | 11 098978 A | 4/1999 |
| JP | 11 100328 A | 4/1999 |
| WO | WO 97/45530 A1 | 12/1997 |

*Primary Examiner*—Herbert J. Lilling
(74) *Attorney, Agent, or Firm*—Alston & Bird LLP

(57) ABSTRACT

The invention concerns lactic acid bacteria with anxiolytic properties and not inducing sedative effect. Said lactic acid bacteria are useful in particular for preparing foods or medicines.

11 Claims, 6 Drawing Sheets

LACTIC ACID BACTERIA WITH ANXIOLYTIC PROPERTIES AND USES THEREOF

Figure 1:
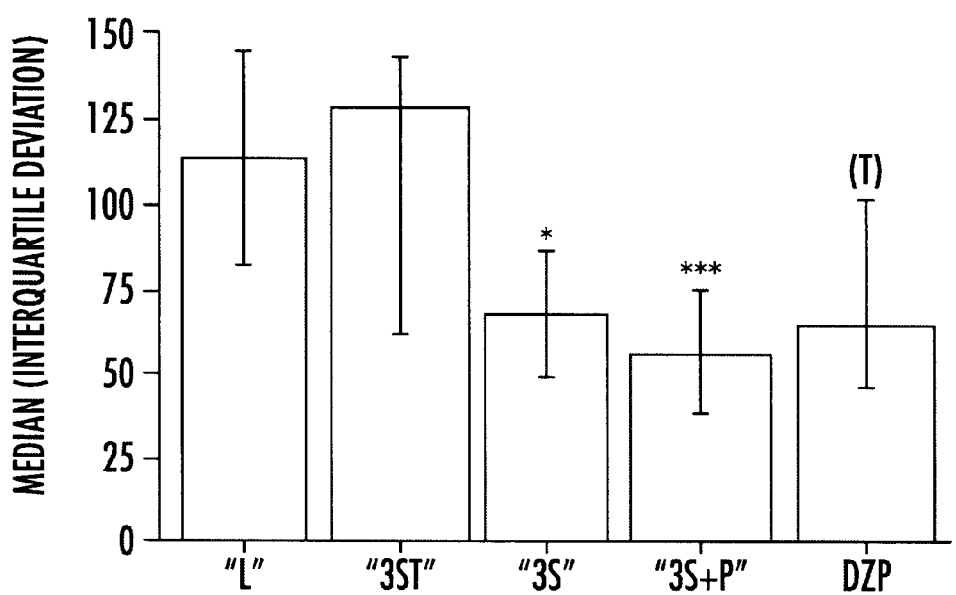

The invention relates to novel strains of lactic ferments and to their use for the production of foods endowed with anxiolitic properties.

Stress, which is a defensive reaction of the body against external attacks, causes in particular at the level of the nervous system, biological disruptions which can develop into various pathological conditions. The latter can manifest themselves directly at the psychological level, in particular in the form of anxiety, and/or can take the form of somatic manifestations, such as high blood pressure, gastric ulcerations and the like. They frequently progress to chronic states.

To treat the consequences of stress, whether involving anxiety or somatic manifestations, anxiolytic, and in particular benzodiazepines, are frequently used. However, these medicaments, which can rapidly cause a phenomenon of addiction, may not be suitable for a long-term treatment. Moreover, their anxiolytic action is accompanied in particular by sedative properties which can cause unwanted side effects.

Some research studies have demonstrated the existence, in milk or in products derived therefrom, of substances endowed with pharmacological properties toward pathological conditions linked to stress. In particular, PCT application WO 98/05343, in the names of CALPIS CO. AND GROUPE DANONE, describes an agent possessing antistress properties manifested by an antihypertensive effect. This agent is obtained by fermenting milk with a lactic acid bacterium of the genus Lactobacillus, in particular Lactobacillus helveticus. It is resistant to sterilization and can be used to prepare foods participating in the prevention and/or treatment of the peripheral (somatic) effects of stress, and which can be consumed in the context of the usual diet, regularly and over long periods. No central, in particular anxiolytic, effect resulting from the administration of this agent is demonstrated in PCT application WO 98/05343.

Application EP 95402697 in the name of: SOCIETE COOPERATIVE LAITIERE AGRICOLE D'ARTOIS ET DES FLANDRES, LA PROSPERITE FERMIERE, describes a decapeptide resulting from the tryptic hydrolysis of casein csl. The parental administration of this decapeptide, or of the tryptic hydrolysate comprising it induces an anxiolytic and anticonvulsant effect of the same type as that by the benzodiazepines. On the other hand, this document provides no information relating to the activity of this hydrolysate when administered orally, and the possibility of incorporating it into foods in order to confer antistress properties on them.

The inventors have now demonstrated, in dairy products fermented by certain strains of lactic acid bacteria, the existence of one or more active ingredients capable of inducing, when they are administered orally, an anxiolytic-type antistress effect, without possessing the sedative properties of the benzodiazepines.

The subject of the present invention is also the use of at least one of the newly isolated and characterized strains of lactic acid bacteria mentioned above, for the production of a nonsedative anxiolytic.

The subject of the present invention is a strain of lactic acid bacterium chosen from the group consisting of:

the *Streptococcus thermophilus* S242 strain deposited on Feb. 24, 1999 in accordance with the Budapest Treaty at the CNCM (Collection Nationale de Cultures de Micro-organismes), 28 rue du Docteur Roux, 75724 Paris, under the number I-2130;

the *Streptococcus thermophilus* S003 strain deposited on 24 February 1999 in accordance with the Budapest Treaty at the CNCM (Collection Nationale de Cultures de Micro-organismes), 28 rue du Docteur Roux, 75724 Paris, under the number I-2129;

the *Lactobacillus gasseri* L012 strain deposited on Feb. 24, 1999 in, accordance with the Budapest Treaty at the. :-CNCM (Collection Nationale de Cultures de Micro-organismes), 28 rue du Docteur Roux, 75724 Paris, under the number I-2131;

the *Lactobacillus acidophilus* L030 strain deposited on Feb. 24, 1999 in accordance with the Budapest Treaty at the CNCM (Collection Nationale de Cultures de Micro-organismes), 28 rue du Docteur Roux, 75724 Paris, under the number I-2132.

The subject of the present invention is also the newly isolated and characterized strains of lactic acid bacteria mentioned above, which can be used for the production of a nonsedative anxiolytic.

The characteristics of the strains of lactic acid bacteria in accordance with the invention are summarized in tables I and II below.

TABLE I

| Strain | S003 | S242 | L012 | L030 |
|---|---|---|---|---|
| CNCM No. | I-2129 | I-2130 | I-2131 | I-2132 |
| Morphology | Fairly large cocci predominantly in the form of long chains and a few in the form of medium and short chains | Small cocci in pairs or in the form of short chains | Small fine bacilli, faintly colored, often coco-bacillary | Medium-sized bacilli, isolated or in the form of short chains |
| Metabolism | Gram + Oxidase:- Catalase:- Facultative aero-anaerobe | Gram + Oxidase:- Catalase:- Facultative aero-anaerobe | Gram + Oxidase:- Catalase:- Nitrate reductase:- Nitrite reductase:- Aero-anaerobe | Gram + Oxidase:- Catalase:- Nitrate reductase:- Nitrite reductase:- Aero-anaerobe |
| Growth T ° | 37–44° C. | 37–44° C. | 37–44° C. | 37–44° C. |

TABLE II

| Strain | S003 | S242 | L012 | L030 |
|---|---|---|---|---|
| CNCM No. | I-2129 | I-2130 | I-2131 | I-2132 |
| Galactose | − | − | + | + |
| D-Glucose | + | + | + | + |
| D-Fucose | − | − | + | + |
| D-Mannose | − | − | + | + |
| N-Acetyl-Glucosamine | − | − | + | + |
| Amygdalin | − | − | + | + |
| Arbutin | − | − | +/− | + |
| Esculin | − | − | + | + |
| Salicin | − | − | + | + |
| Cellobiose | − | − | + | + |
| Matose | − | − | + | + |
| Sucrose | + | + | + | + |
| Threalose | − | − | + | + |
| β-Gentobiose | − | − | + | + |
| D-Tagatose | − | − | + | − |
| D-Turanose | − | − | − | + |
| Lactose | + | + | + | + |

TABLE II-continued

| Strain | S003 | S242 | L012 | L030 |
| --- | --- | --- | --- | --- |
| CNCM No. | I-2129 | I-2130 | I-2131 | I-2132 |
| D-Raffinose | − | − | − | + |
| Melibiose | − | − | − | + |
| α-Methyl-D-Glucoside | − | − | − | + |

The present invention relates in particular to the use, for the production of a nonsedative anxiolytic, of at least one *Streptococcus thermophilus* strain chosen from the S242 strain and the S003 strain, combined with the *S. thermophilus* S147 strain deposited at the CNCM on Dec. 30, 1994 under the number I-1520.

The present invention also relates to lactic ferments comprising at least one strain in accordance with the invention, advantageously combined with another strain of lactic acid bacterium.

According to a preferred embodiment of a lactic ferment in accordance with the invention, it comprises at least the *S. thermophilus* S242 strain and/or the *S. thermophilus* S003 strain, advantageously combined with the *S. thermophilus* S147 strain.

The subject of the present invention is also a non-sedative anxiolytic comprising at least one strain of lactic acid bacterium in accordance with the invention as defined above, or capable of being obtained from a culture of said strain.

For the production of a nonsedative anxiolytic in accordance with the invention, at least one strain of lactic acid bacterium in accordance with the invention is cultured; in particular a lactic ferment comprising at least the *S. thermophilus* S424 strain and/or the *S. thermophilus* S003 strain advantageously combined with the *S. thermophilus* S147 strain, and optionally with the *L. gasseri* L012 strain and/or the *L. acidophilus* L030 strain, is cultured in an appropriate medium, that is to say a medium comprising at least one substrate allowing the growth of said bacteria. Said culture medium is preferably milk or a milk-based medium. It may be chosen in particular from the milks of the various species of mammals, optionally semiskimmed or skimmed, the products resulting from the dilution or the concentration of these milks, such as for example ultrafiltration of diafiltration retentates, milk-based media, such as for example bases for milk-based foods, bases for yogurt and the like. These milks may, in addition, be supplemented with, for example, lactose, minerals, vitamins, fatty substances or otherwise, hydrophilic milk solids, soybean proteins, plant extracts and the like.

This medium is inoculated with a culture comprising at least one strain of lactic acid bacterium in accordance with the invention, preferably comprising $10^7$ to $10^9$ bacteria/ml. The optimum culture conditions vary according to the strain or the mixture of strains involved. For example, if the culture for inoculation consists of a strain or a mixture of strains of *Streptococcus thermophilus*, the culture will be carried out for about 24 h and the optimum culture temperature will be between 30 and 44° C.; if the culture for inoculation consists of a strain or a mixture of strains of *L. acidophilus* or of *L. gasseri*, the culture will be carried out for about 16 h and the optimum culture temperature will be between 37 and 44° C. In the case where the culture for inoculation combines at least one *Streptococcus thermophilus* strain with at least one *L. acidophilus* or *L. gasseri* strain, the culture will be carried out for 16 to 24 h, and the optimum culture temperature will be between 37 and 44° C.

The bacterial culture thus obtained possesses the properties of a nonsedative anxiolytic in accordance with the invention.

The nonsedative anxiolytics in accordance with the invention are active when administered orally. Regular administration thereof causes, after a few days, a reduction in anxiety, with no reduction in activity; it can be extended for a very long period, with no addiction effect, and without the appearance of unfavorable side effects. These properties, as well as the fact that it is possible to obtain them from micro-organisms belonging to species commonly used in the food industry, and from raw materials which are also intended for dietary use, make it possible to use them in the context of the manufacture of foods or dietary supplements, whose consumption exerts a beneficial effect in the context of the treatment or of the prevention of stress-related pathological states.

The subject of the present invention is also the food products or dietary supplements comprising a non-sedative anxiolytic in accordance with the invention.

These food products may be in particular products comprising at least one strain of lactic acid bacterium or a lactic ferment in accordance with the invention. They are in particular products which can be obtained by fermenting milk or a milk-based medium with said strain of said ferment. Food products in accordance with the invention can also be prepared by adding to any food which is fermented or otherwise a preparation comprising a nonsedative anxiolytic in accordance with the invention.

The beneficial effects of the foods in accordance with the invention generally appear starting from a dose of 5 ml/day/kg of weight, in the case of a fermented milk containing a total population (which may consist of one or more strains of bacteria in accordance with the invention) of lactic acid bacteria in accordance with the invention of at least $10^5$ CFU/ml. Substantially higher doses can however be taken, with no harmful side effects.

The present invention will be understood more clearly with the aid of the additional description which follows, which refers to nonlimiting examples illustrating the anxiolytic properties of fermented dairy products obtained in accordance with the invention.

EXAMPLE 1

Preparation of Various Test Dairy Products

The strains and ferments used in the various experiments which follow are the following:

*S. therimophilus* S242 strain
*S. thermophilus* S147 strain
*S. thermophilus* S003 strain
Ferment F042 (ferment combining the 3 strains S242, S147, S003 of *S. thermophilus*)
*L. gasseri* L012 strain
*L. acidophilus* L030 strain.

Manufacture of the Products:

UHT milk containing 0% fat was treated at 95° C. for 10 minutes, and then cooled to 37 or 44° C. depending on the temperature for the fermentations, before being inoculated with active cultures of the strains used to obtain the desired preparation.

The inoculation with the *S. thermophilus* S242, S147 and S003 strains used individually, is carried out at the rate of 1% (v/v) of a culture containing $10^8$ to $10^9$ CFU/ml of sterile milk supplemented with yeast autolysate (3 h at 44° C.).

The inoculation with the ferment S042 is carried out at the rate of 30 g/100 l of a frozen concentrated mixture between $10^8$ and $10^9$ CFU/ml of the S242, S147 and S003 strains. The incubation is carried out at 44° C.; when the pH reaches about 4.5, the preparation is transferred to 4° C. and stored at this temperature pending use.

The bacterial populations at the end of the fermentation in the products fermented by the strains separated are: *Streptococcus thermophilus* S242: $1.2\times10^9$ CFU/ml; *Streptococcus thermophilus* S147: $1.8\times10^9$ CFU/ml; *Streptococcus thermophilus* S003: $1.3\times10^7$ CFU/ml.

In the product fermented by the F042 mixture, the *Streptococcus thermophilus* (S242+S147+S003) concentration is $1.9\times10^8$ CFU/ml.

The inoculation with the *L. acidophilus* L012 and L030 strains is carried out at the rate of 3% (v/v) of a culture containing $10^8$ to $10^9$ CFU/ml in neutral MRS medium (16 h at 37° C.). The incubation is carried out at 37° C.; when the pH reaches a value of between 4.5 and 5.9, the preparation is transferred to 40° C., and stored at this temperature pending use.

The filtered whey of the milk fermented by the ferment F042 is prepared by centrifuging 500 ml of fermented milk at 10 000 rpm (Sorval RC5B centrifuge, GSA rotor) twice 15 minutes and then by filtering the supernatant over a NALGENE filter made of cellulose nitrate (HIGH-BINDING PROTEIN) 0.45 µm and then 0.22 µm.

EXAMPLE 2

Evaluation of the Anxiolytic Effect of a Mixture of 3 Thermophilic Streptococci

The Products Tested are the Following:

3S: milk fermented by the ferment F042 (comprising 3 *S. thermophilus* S242, S147, S003)

3S+P: milk fermented by the ferment F042+ Passionflower

3ST: milk fermented by the ferment F042 and then thermized at 73° C. for 30 seconds with homogenization at 100 bar.

L: control milk sterilized at 130° C. for 30 seconds.

The anxiolytic effect is evaluated using the Conditioned Defensive Burying model, which was developed from the procedure by J. P. PINEL and D. TREIT (PINEL and TREIT, J. Comp. & Physiol. Psychol., 92, 708–712, 1978; TREIT et al., Pharmacol. Biochem. Behav., 15, 619–626, 1981). This model uses the natural propensity of most rodents to bury themselves from a stressful source of stimulus (TREIT, Pharmacol. Biochem. Behav., 22, 1, 47–52, 1985; MEERT and COLPAERT, Psychopharmacology, 88, 445–450, 1986; CRAFT et al., Pharmacol. Biochem. Behav., 30, 3, 775–780, 1988; TREIT, Pharmacol. Biochem. Behav., 36, 203–205, 1990).

Animals

Seventy two SPF Wistar/AF male rats (IFFA-CREDO breeding center, 69—St-Germain sur l'Arbresle, France) weighing 320 to 340 g were used. On reception, the rats were weighed, marked and divided into groups of 4 in type F polycarbonate cages (48×27×20 cm, U.A.R., 91—Epinay-Sur-Orge, France). The animals were stalled in an air-conditioned animal house, at a temperature of 22–24° C. Food (M25 biscuits, Ets PIETREMENT, 77—Provins, France) and drink were available to the rats ad libitum. They were subjected to a light-darkness cycle of 12 hours (light from 24 h to 12 h).

After a week's familiarization with the laboratory conditions, the 72 rats were randomly divided into 6 groups (n=12). The rats in the different groups were all handled in the same way and under the same conditions.

Materials

Experimental Cage

Habituation and the tests were carried out in a transparent cage having the dimensions 44×28×18 cm, whose base is covered with sawdust over a thickness of 5 cm. In the middle of a lateral face, an orifice allows the attachment of an electric probe, 2 cm above the level of the sawdust.

Electric Probe

It is a probe made of plexiglas having the dimensions 7×2×0.5 cm, covered with a copper printed circuit in which the gap between the wires is 1 mm, chosen so that one leg of the rat coming to rest on the probe easily makes contact between them, thus allowing the passage of current.

Electrical Apparatus

The probe is connected to a manually triggered generator of electric shocks of 0 to 8 mA (OPEN-SYSTEMS, 54—Maxeville, France).

Recording and Evaluation of the Behavioral Sequences

In the faintly illuminated experimental room, a video camera was placed in front of the cage of the setup, at a distance of one meter. The camera is connected to a video recorder and to a control monitor, which are placed in an adjacent room with the electric shock generator.

Experimental Procedure

The experiment was carried out according to a double blind design.

Habituation

During the 2 days preceding the first test, the rats were transported from the animal house to the experimental room and introduced into the experimental device in order to habituate them to both the handling and to the cage of the device in the absence of the electrode. Each group of 4 rats was placed in the device for 20 minutes. The sawdust is changed, leveled to a uniform height of 5 cm, before the period of habituation of each of the groups.

Experience

The Conditioned Defensive Burying test is carried out in the first 5 hours of the dark phase, a phase during which the rats are the most active.

The electric probe is inserted into the cage before the beginning of the first test. Each rat is placed in the experimental cage on the side opposite the probe.

During the first test (test 1), a single electric shock, of low intensity (2 mA) is delivered to the animal when it places a hind leg for the first time on the probe.

Following the electric shock, the behavior of each rat is recorded for 5 minutes. During the next two tests (tests 2 and 3), the rat is again placed in the experimental cage in the presence of the inactive probe. The probe is cleaned after each rat and the sawdust is changed and leveled to a uniform height of 5 cm before the test session for each cage of rats.

Administration of the Products

The products L, 3ST, 3S and 3S+P were orally administered daily at the same times, at the doses of 5 ml/kg by means of syringes provided with intragastric forced-feeding probes (HARVARD APPARATUS, 91—Les Ulis, France). The burying tests (test 1 on day 6 and test 2 on day 8) were carried out 6 hours after the administration of the products.

The positive control is diazepam (3 mg/kg), which was suspended in an aqueous solution of methyl cellulose at 1% and was orally administered daily, for the same period. On the test days, it was administered 1 hour before the burying test.

The four rats of each cage each received a different product.

Variables duration of burying for the probe: the burying sequences are remarkably stereotyped after the shock; the rat faces the electric probe and sends the sawdust in its direction by a rapid alternating movement of the hind legs;

number of writhing movements in relation to the probe: the rat stops a few centimeters from the probe and extends its neck in order to bring the muzzle closer to the probe;

number of approaches to the probe: every approach of the rat's head in the direction of the probe to a distance of less than 3 cm;

number of flights in relation to the probe: every hasty flight of the rat following an approach to or a contact with the probe;

percentage of approaches to the probe followed by flights=(number of flights/number of approaches)×100.

Statistical Analysis

The data were classified in increasing order for the following variables: duration of burying, number, of writhing movements and percentage of approaches followed by flights. Within the various variables, a rank was attributed to each data and the rank sum constitutes the overall stress score for each rat.

The KRUSKAL-WALLIS test was used to demonstrate the existence of heterogeneity among the groups. The MANN-WHITNEY test served to compare the groups DZP, 3ST, 3S and 3S+P with the control L. The results are expressed as a median and interquartile deviation (Lower Quartile —Upper Quartile).

The statistical and graphical processes were carried out using the STATVIEW 4.1 and DELTAGRAPH PRO 3.5 software packages.

Results

Overall Stress Score During Test 1

The results of this test are illustrated by FIG. 1.

Legend to FIG. 1

L: Control sterile milk

3ST: Milk fermented by the ferment F042 and then thermized

3S: Milk fermented by the ferment F042

3S+P: Milk fermented by the ferment F042+ Passionflower

DZP: Diazepam

Mann-Whitney test: *p<0.05 vs. L, * * * p<0.005 vs. L and (T) trend vs. L (p<0.07).

During test 1, the products 3S and 3S+P significantly reduce the overall stress score compared with the control product L.

The product 3ST is not significantly different from the control product L. Diazepam tends to reduce the overall stress score compared with the control L.

During test 1, apart from diazepam, no product showed a sedative effect.

Overall Stress Score During Test 2

Figure 2:
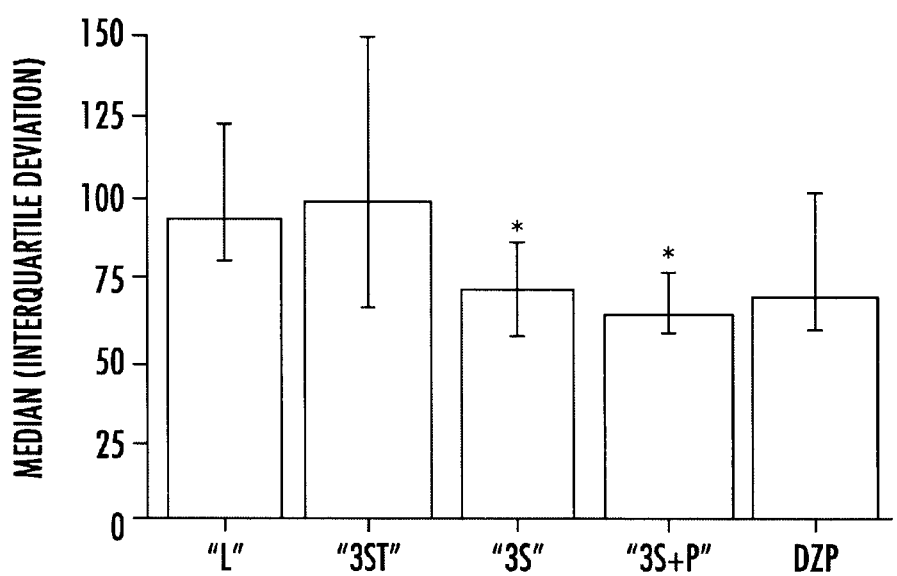

The results of this test are illustrated by FIG. 2.

Legend to FIG. 2

L: Control sterile milk

3ST: Milk fermented by the ferment F042 and then thermized

3S: Milk fermented by the ferment F042

3S+P: Milk fermented by the ferment F042+ Passionflower

DZP: Diazepam

Mann-Whitney test: p>0.05 vs. L.

During this test, the products 3S and 3S+P significantly reduce the overall stress score compared with the control product L.

The effects of the product 3ST and of diazepam are not significantly different from the product L.

Conclusions

During tests 1 and 2, the products 3S and 3S+P significantly reduce the overall stress score compared with the control product L. The product 3ST shows no activity against stress during the two tests compared with the control product.

Diazepam, administered at the dose of 3 mg/kg p.o., for 6 days before test 1, showed only a trend to reduce the overall stress score compared with the control. During test 2, it shows no effect which is statistically different from that of the control. This is a habituation phenomenon specific to products of the benzodiazepine family.

It can be concluded that the products 3S and 3S+P have a significant antistress activity whereas the effect of the product 3ST is not different from that of the control. The phenomenon of tolerance observed with diazepam is not observed with the products 3S and 3S+P.

No sedation problem was revealed with these two products.

EXAMPLE 3

Anxiolytic Effect of Milks Fermented by Various Lactic Acid Bacteria

The products tested are the following:

SC008 1.1: milk fermented by S. thermophilus S242;

SC008 1.2: milk fermented by S. thermophilus S147;

3S: milk fermented by the ferment F042 (S242+S147+ S003);

SC008 1.5: filtered whey of milk fermented by the ferment F042;

L: control sterile milk (95° C. 10 min);

SC008 1.8: milk fermented by L. gasseri L012;

SC008 1.10: milk fermented by L. acidophilus L030;

SC008 1.12: milk fermented by S. thermophilus S003.

The tests were carried out according to the protocol described in example 2 above, on one hundred and fifty eight SPF Wistar/AF males (IFFA-CREDO breeding center, 69—St Germain sur Arbresles, France) weighing 260 to 280 g. After a week's familiarization with the laboratory conditions, the rats were randomly divided into 13 treatment groups. The rats of the various groups were handled in the same manner and under the same conditions.

Administration of the Products

All the products were orally administered daily for 6 days at the same times at the doses of 5 ml/kg using syringes equipped with intragastric forced-feeding probes (HARVARD APPARATUS, 91—Les Ulis, France). On the day for the test, they were administered 6 hours before the burying test.

Diazepam (1 mg/kg, p.o., on days 1 and 2; 2 mg/kg p.o., on days 3 and 4 and 3 mg/kg, p.o., on days 5 and 6) was suspended in a volume of 5 ml of aqueous solution of methyl cellulose at 1%. On the day for the test, it was administered 1 hour before the burying test.

To avoid interference, all the rats of the same cage received the same product.

Variables

In addition to the variables already described in example 2, the following variables of the sedative effect are studied:
- number of writhings: the rat adopts the vertical position while resting on its hind legs;
- number of passes from one side of the cage to another.

Results

Overall Stress Score

Compared with the product L, the products SC008 1.1, 3S, SC008 1.8, SC008 1.10, SC008 1.12 and diazepam induce significantly lower overall stress scores.

The stress scores induced by the products SC008 1.2 and SC008 1.5 are not significantly different from the control product. The results are illustrated by FIG. 3.

Figure 3:
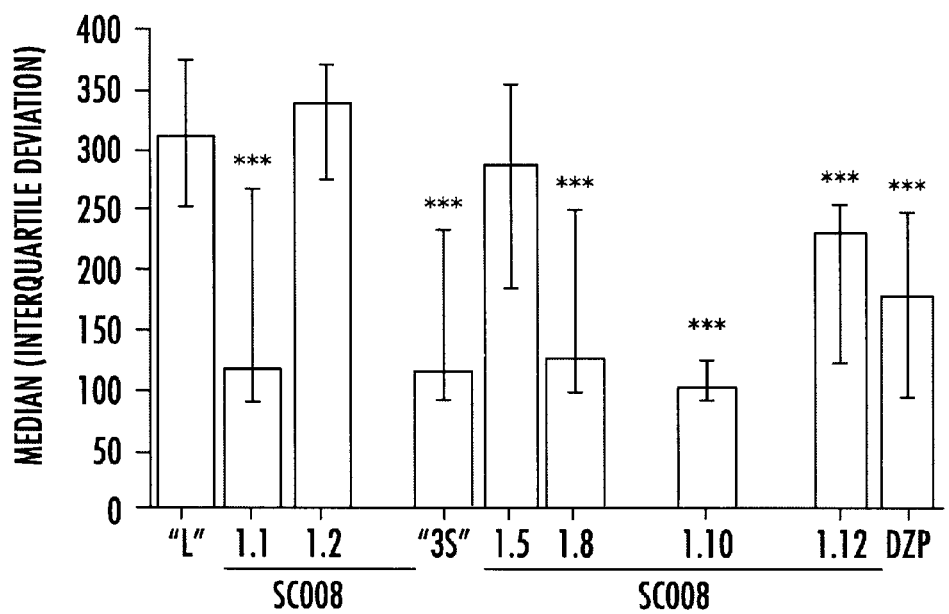

Legend to FIG. 3:
L: Control sterile milk (95° C. 10 min);
SC008 1.1: milk fermented by S. thermophilus S242;
SC008 1.2: milk fermented by S. thermophilus S147;
3S: milk fermented by the ferment F042 (S242+S147+ S003);
SC008 1.5: filtered whey of milk fermented by the ferment F042;
SC008 1.8: milk fermented by L. gasseri L012;
SC008 1.10: milk fermented by L. acidophilus L030;
SC008 1.12: milk fermented by S. thermophilus S003;
DZP: Diazepam.
Mann-Whitney test:
* * * $p<0.005$ vs.L.

Sedative Effect of the Products 3S and SC008 1.10

The sedative effect of the products 3S and SC008 1.10 compared with the control product L is evaluated on the basis of the locomotive and exploratory activity.

Number of Writhings During the Test

A heterogeneity is observed in the number of writhings obtained with the products 3S, SC008 1.10 and L (Kruskal-Wallis test: $H_{(d.o.f.}$ 2)=6.170; p<0.05). The product 3S causes a significant increase in the number of writhings compared with the control product L (Mann-Whitney test: U=65; p<0.05). The product SC008 1.10 tends to increase the number of writhings compared with the control product L (Mann-Whitney test: U=73; p<0.07).

Number of Passings From One Side of the Cage to Another

No significant difference is observed in the number of passings from one side of the cage to another in the case of the products 3S, SC008 1.10 and in that of the control product L (Krusdal-Wallis test: $H_{(d.o.f.}$ 2)0.983: N. S.).

Conclusion

Under the experimental conditions, on the basis of the overall stress score, SC008 1.1, 3S, SC098 1.8, SC008 1.10, SC008 1.12, and diazepam show a significant antistress activity compared with the control product L. The products SC008 1.2 and SC008 1.5 exhibit no significant antistress activity compared with the control product L.

On the basis of the locomotive and exploratory activity and compared with the control L, no sedative effect was observed with the fermented milks showing an antistress activity.

EXAMPLE 4

Determination of the Optimun Duration of Administration of the Products by the Oral Route The test products are the following:
3S: Milk fermented by the ferment F042 (S242+S147+ S003);
L: Control sterile milk (95° C. 10 min).

The tests were carried out according to the protocol described in example 2 above, on seventy two SPF Wistar/ AF males (Iffa-Credo breeding center, 69—St Germain sur Arbresles, France) weighing 260 to 280 g. After a week's familiarization with the laboratory conditions, the rats were randomly divided into 6 treatment groups. The rats of the various groups were handled in the same manner and under the same conditions.

Administration of the Products

The products were orally administered daily for 1, 3 and 6 days at the doses of 5 ml/kg using syringes equipped with intragastric forced-feeding probes (HARVARD APPARATUS, 91—Les Ulis, France). On the day of the test, they were administered 6 hours before the burying test.

The four rats of each cage all received the same product.

Results

Overall Stress Score

When administered as a single dose or daily for 3 days before the test, the product 3S induces an overall stress score which is statistically equivalent to that of the control product L.

When administered daily for 6 days before the test, the product 3S induces an overall stress score which is significantly less than that obtained with the product L.

Figure 4:
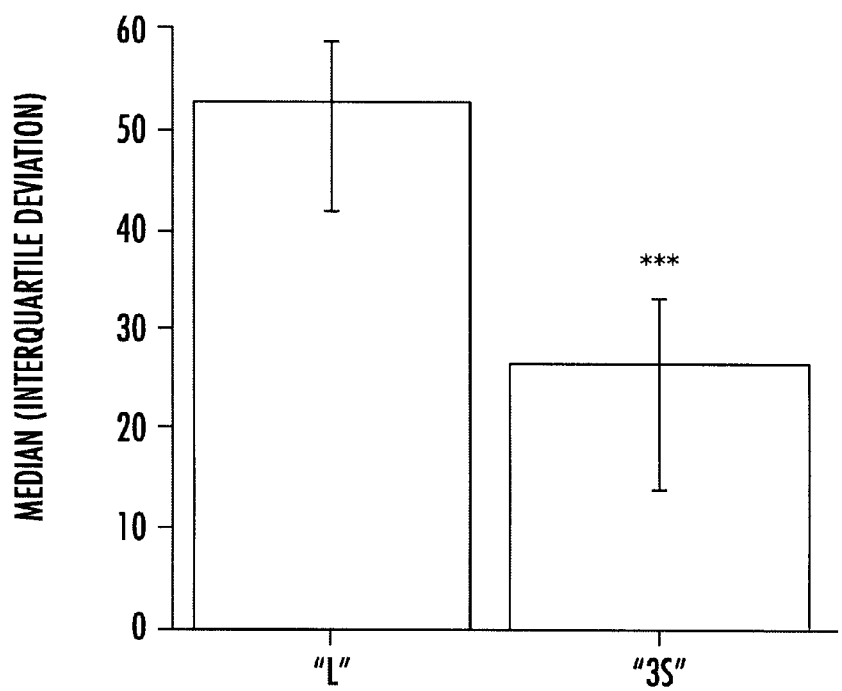

The results are illustrated by FIG. 4.

Legend to FIG. 4:
L: Control sterile milk (95° C. 10 min)
3S: Milk fermented by the ferment F042 (S242+S147+ S003)
Mann-Whitney test:
* * * $0<0.005$ vs. L.

Conclusion

Under the experimental conditions described above, a daily administration of the product 3S for 6 days is necessary to show a significant antistress activity compared with the control product L.

EXAMPLE 5

Determination of the Optimun Time for Oral Administration of the Products

The test products are the following:
3S: Milk fermented by the ferment F042 (s242+S147+ S003)
L: Control sterile milk (95° C. 10 min).

The tests were carried out according to the protocol described in example 2 above, on one hundred and eight SPF Wistar/AF males (Iffa-Credo breeding center, 69—St Germain sur Arbresles, France) weighing 260 to 280 g. After a week's familiarization with the laboratory conditions, the rats were randomly divided into 9 treatment groups. The rats of the various groups were handled in the same manner and under the same conditions.

Administration of the Products

Prior to the test, the products were orally administered daily for 6 days at the doses of 5 ml/kg using syringes equipped with intragastric forced-feeding probes (Harvard Apparatus, 91—Les Ulis, France). At the end of this period, the burying test is carried out 1, 3 or 6 or 24 hours after the last dose.

Diazepam (1 mg/kg, p.o., on days 1 and 2; 2 mg/kg p.o., on days 3 and 4 and 3 mg/kg, p.o., on days 5 and 6) is administered in a volume of 5 ml of aqueous solution of methyl cellulose at 1%. The last administration is carried out 1 hour before the burying test. All the four rats of each case received the same product.

Results

Overall Stress Score

When the administration is carried out one hour before the test, the product 3S induces an overall stress score equivalent to that obtained with the control product L. The overall stress score of diazepam is significantly lower than that of the control product L.

When the administration is carried out 3 hours before the test, the product 3S induces an overall stress score which is not statistically different from that of the control product L.

When the administration is carried out 6 or 24 hours before the test, the product 3S shows an overall stress score which is significantly lower than that obtained with the control product L.

Figure 5:
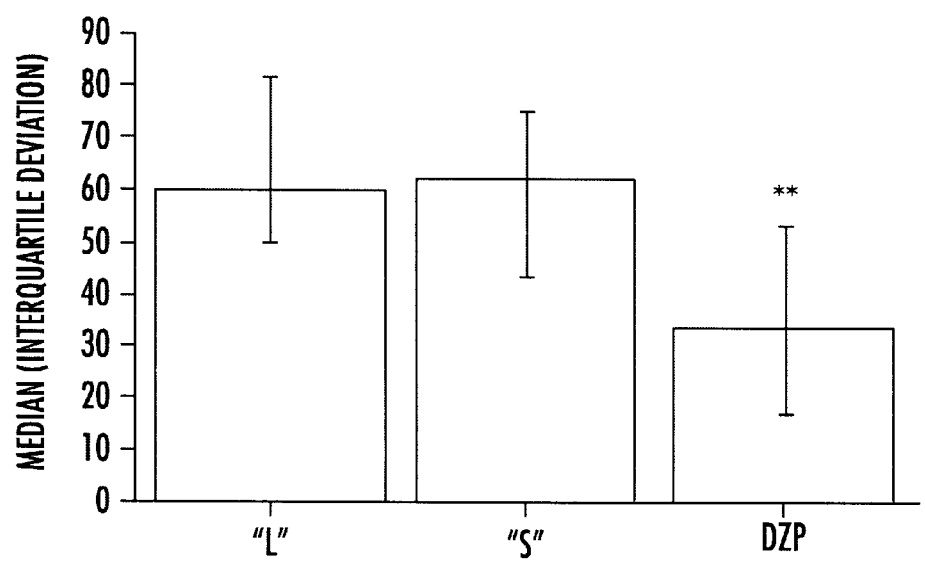
Figure 6:
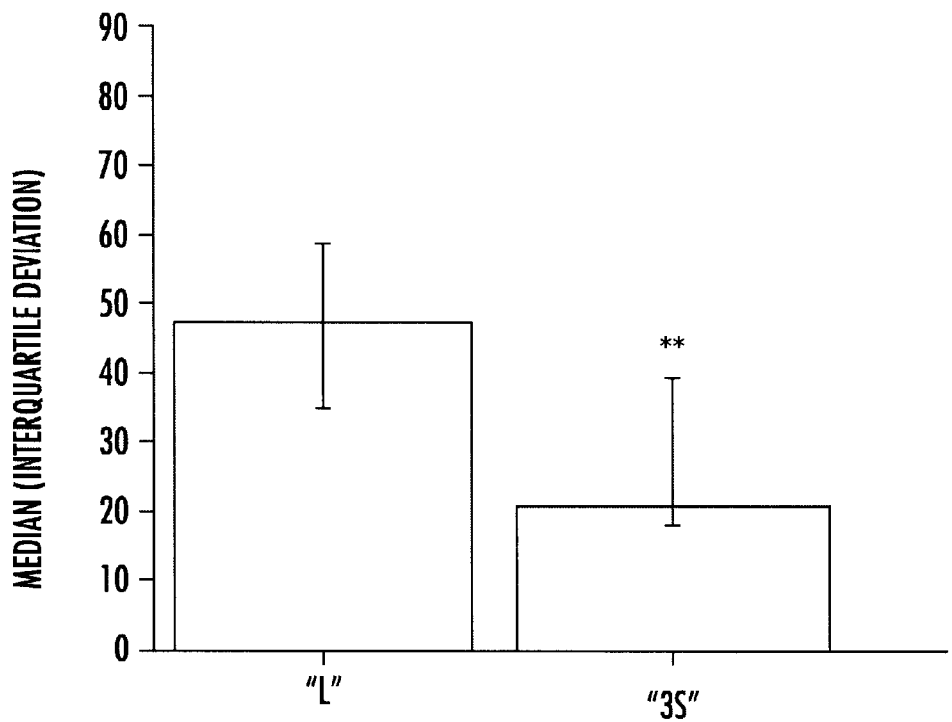

The results at 1 hour and 6 hours are illustrated by FIGS. 5 and 6.

Legend of FIGS. 5 and 6:

L: Control sterile milk (95° C. 10 min)

3S: Milk fermented by the ferment F042 (S242+S147+S003)

DZP: Diazepam

Mann-Whitney test:

* * $p<0.01$ vs. L.

Conclusion

Under the experimental conditions described above and on the basis of the overall stress score, the antistress activity manifests itself between 6 and 24 hours after the administration of the product 3S.

EXAMPLE 6

Search for the Decapeptide Derived From the Tryptic Hydrolysis of Casein αs1 in a Product Fermented with the 3S Mixture The presence of the decapeptide described in application EP 95402697 was sought in the product 3S. The analysis was carried out by reversed phase HPLC on C18 (the separation of the peptides is based on their hydrophobicity).

The analysis was carried out on a NUCLEOSIL C18-10 μ "precolumn" —100 mm×4.6 mm, followed by a NUCLEOSIL C18-3 μ analytical column—150 mm×4.6 mm, using the following gradient:

A: TFA 0.1% in $H_2O$

B: 90% $CH_3CN$+10% TFA 0.1% in $H_2O$

The elution is carried out as indicated in table III below.

TABLE III

| Time   | A  | B  |
|--------|----|----|
| 0 min  | 90 | 10 |
| 10 min | 60 | 40 |
| 40 min | 60 | 40 |
| 45 min | 90 | 10 |
| 60 min | 90 | 10 |

The detection is carried out at 215 nm.

Under these conditions, the retention time for the decapeptide deposited on the column is 29 min.

Preparation of the Test Sample:

Product 3S+20% $CH_3CN$; stirring and then centrifugation 20 min 10 000 rpm.

Recovery of the soluble phase and then filtration on GELMAN 0.45 μ GHP-GF filter (low protein binding) before injection of 100 μl of the filtrate onto the HPLC column.

No peak corresponding to the retention time of the desired decapeptide was found in the filtrate of the product 3S.

What is claimed is:

1. A method for the production of a nonsedative anxiolytic which comprises culturing in an appropriate medium at least one strain of lactic acid bacterium chosen from:

the *S. thermophilus* S242 strain deposited at the CNCM on Feb. 24, 1999 under the number I-2130;

the *S. thermophilus* S003 strain deposited at the CNCM on Feb. 24, 1999 under the number I-2129;

the *L. gasseri* L012 strain deposited at the CNCM on Feb. 24, 1999 under the number I-2131;

the *L. acidophilus* L030 strain deposited at the CNCM on Feb. 24, 1999 under the number I-2132.

2. A strain of lactic acid bacterium which can be used for the production of a nonsedative anxiolytic, chosen from:

the *S. thermophilus* S242 strain deposited at the CNCM on Feb. 24, 1999 under the number I-2130;

the *S. thermophilus* S003 strain deposited at the CNCM on Feb. 24, 1999 under the number I-2129;

the *L. gasseri* L012 strain deposited at the CNCM on Feb. 24, 1999 under the number I-2131;

the *L. acidophilus* L030 strain deposited at the CNCM on Feb. 24, 1999 under the number I-2132.

3. The method as claimed in claim 1, wherein at least one *Streptococcus thermophilus* strain chosen from the S242 strain and the S003 strain is combined with the *S. thermophilus* S147 strain deposited at the CNCM on Dec. 30, 1994 under the number I-1520.

4. A lactic ferment comprising at least one *S. thermophilus* strain chosen from the S242 strain deposited at the CNCM on Feb. 24, 1999 under the number I-2130 and the S003 strain deposited at the CNCM on Feb. 24, 1999 under the number I-2129.

5. The lactic ferment as claimed in claim 4, comprising, in addition, the *S. thermophilus* S147 strain deposited at the CNCM on Dec. 30, 1994 under the number I-1520.

6. The lactic ferment as claimed in claim 4 which comprises, in addition, at least one strain of lactic acid bacterium chosen from the group consisting of:

the *L. gasseri* L012 strain deposited at the CNCM on Feb. 24, 1999 under the number I-2131;

the *L. acidophilus* L030 strain deposited at the CNCM on Feb. 24, 1999 under the number I-2132.

7. A food product or a dietary supplement comprising a nonsedative anxiolytic obtained by fermenting a milk or a milk based product with at least one strain of lactic acid bacterium as claimed in claim 2.

8. The lactic ferment as claimed in claim 5 which comprises, in addition, at least one strain of lactic acid bacterium chosen from the group consisting of:

the *L. gasseri* L012 strain deposited at the CNCM on Feb. 24, 1999 under the number I-2131;

the *L. acidophilus* L030 strain deposited at the CNCM on Feb. 24, 1999 under the number I-2132.

9. The food product or the dietary supplement as claimed in claim 7, which is obtained by fermenting milk or a milk-based medium with a lactic ferment as claimed in claim 4.

10. The food product or the dietary supplement as claimed in claim 7, which is obtained by fermenting milk or a milk-based medium with a lactic ferment as claimed in claim 5.

11. The food product or the dietary supplement as claimed in claim 7, which is obtained by fermenting milk or a milk-based medium with a lactic ferment as claimed in claim 6.

* * * * *